United States Patent [19]
Benton et al.

[11] Patent Number: 6,000,290
[45] Date of Patent: Dec. 14, 1999

[54] QUICK-CONNECT INDUSTRIAL PROCESS SENSOR

[75] Inventors: Barry W. Benton, Orange; Wayne B. Wood, Silverado, both of Calif.

[73] Assignee: Rosemount Analytical Inc., Irvine, Calif.

[21] Appl. No.: 08/968,205

[22] Filed: Nov. 12, 1997

[51] Int. Cl.$^6$ .................................................. G01M 19/00
[52] U.S. Cl. .............................................................. 73/866.5
[58] Field of Search ................................. 73/866.5, 19.1, 73/756; 374/208; 324/724, 692; 204/416, 431; 422/82.01–82.04, 90

[56] References Cited

U.S. PATENT DOCUMENTS

| | | | |
|---|---|---|---|
| 4,537,071 | 8/1985 | Waterman | 73/866.5 |
| 4,862,598 | 9/1989 | Barlow et al. | 33/613 |
| 5,201,226 | 4/1993 | John, Jr. et al. | 73/866.5 X |
| 5,342,126 | 8/1994 | Heston et al. | 374/208 |
| 5,450,766 | 9/1995 | Holt | 73/866.5 |
| 5,761,978 | 6/1998 | Nordlot | 83/259 |

OTHER PUBLICATIONS

"Kamlok® Twin–Cam® Quick–Disconnect Couplings," CIVACON™, Product Brochure KAM–Pl, Effective Feb. 1, 1995, 8 pages.

"Twist–Lock Electrodes for pH and ORP Application," Van London Company, Inc. Product Brochure, (Undated). But b, Feb. 1998 2 pages.

"pH/ORP Sensors—Specifications, Dimensions," TBI–Bailey Controls Company, Product Brochure, Feb. 1, 1994, 4 pages.

Model FU20 and FU25—pH/redox and temperture sensor, Johnson Yokogawa, Product Brochure GS 12B6J3–U–H, 2nd Edition, Nov. 1994, 3 pages.

*Primary Examiner*—Thomas P. Noland
*Attorney, Agent, or Firm*—Westman, Champlin & Kelly, P.A.

[57] ABSTRACT

An industrial process sensor includes a proximal end, a distal end, a longitudinal axis and an outer diameter surface. A cam follower surface is recessed into the outer diameter surface. A diameter reduction is formed on the outer diameter surface, between the cam follower surface and the distal end. The diameter reduction defines an annular process sealing shoulder that faces the distal end and lies in a plane intersecting the longitudinal axis. A sensor element is carried at the distal end. A cable is electrically coupled to the sensor element and extends from the proximal end.

19 Claims, 4 Drawing Sheets

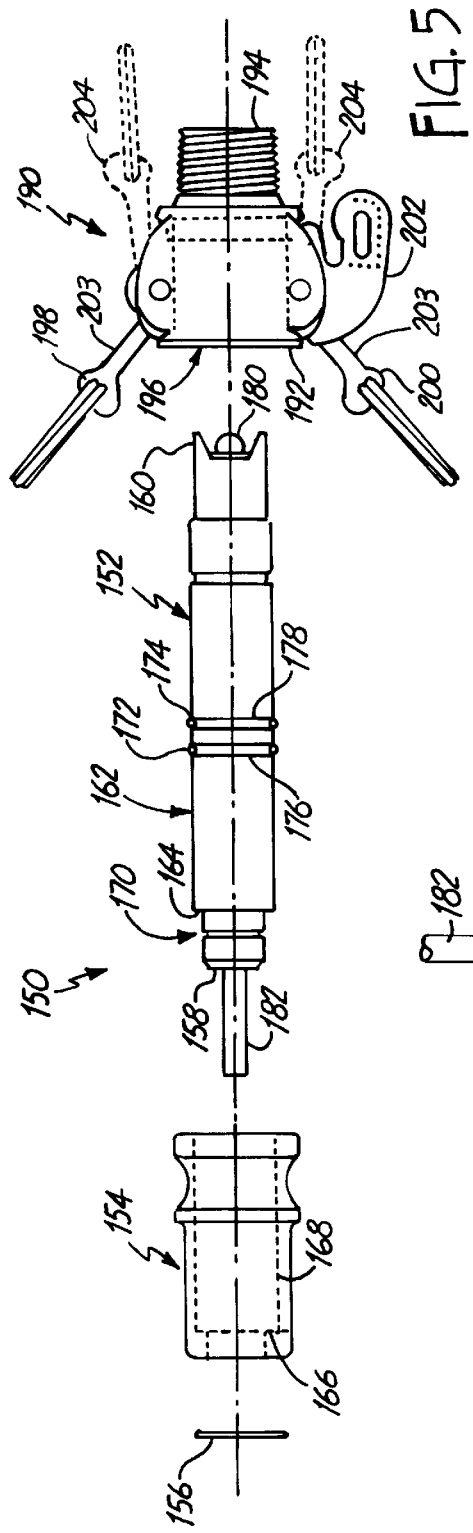
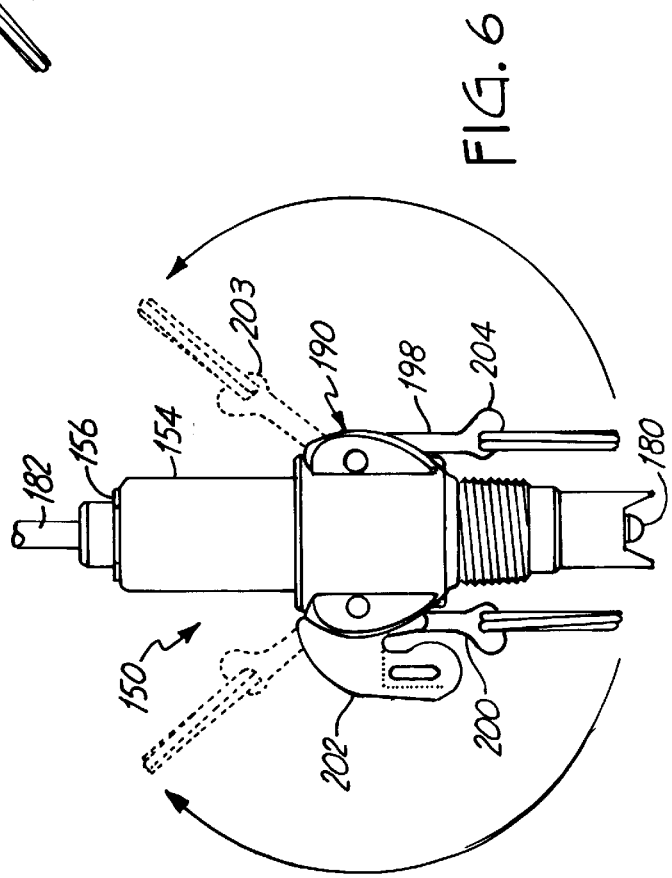
FIG. 5
FIG. 6

QUICK-CONNECT INDUSTRIAL PROCESS SENSOR

BACKGROUND OF THE INVENTION

The present invention relates to an industrial process sensor configured for mounting to a process through a cam arm locking coupler.

Industrial process sensors are used in a variety of applications for measuring characteristics, such as pH, of a sample solution. Sensor installations are often positioned in difficult to access locations, and installation may require a ladder or protective clothing. Sensor installations frequently use male pipe threads for securing the sensor into a process threaded pipe or tank fitting. With a threaded fitting, multiple revolutions of the sensor and its attendant electrical cable are required to install or remove the sensor. Installation and removal with threaded fittings usually require a tool and are time consuming and potentially damaging to the sensor.

Alternative fittings have been used to alleviate these problems. These fittings include a union nut fitting, a bolted flange fitting, a compression fitting, a bayonet fitting and a quarter-turn fitting. However, these fittings still require the use of tools or partial rotation of the sensor. For example, a typical bayonet fitting includes engaging pins projecting radially from the sensor surface. The engaging pins pass through slots in the process fitting, which are parallel to the long axis of the sensor, until the engaging pins align with channels formed on the inner diameter surface of the fitting. The sensor is then rotated to slide the pins within the channels, thereby locking the sensor into place. Also, these fittings typically do not provide a visually perceptible indication of a proper seal.

SUMMARY OF THE INVENTION

The industrial process sensor of the present invention includes a proximal end, a distal end, a longitudinal axis and an outer diameter surface. A cam follower surface is recessed into the outer diameter surface. A diameter reduction is formed on the outer diameter surface, between the cam follower surface and the distal end. The diameter reduction defines a process sealing shoulder that faces the distal end and lies in a plane intersecting the longitudinal axis. A sensor element is carried at the distal end. A cable electrically couples to the sensor element and extends from the proximal end.

The industrial process sensor of the present invention is mounted to a process through a cam arm locking coupler. The coupler includes a bore and a diameter reduction within the bore which defines a second process sealing shoulder that engages the first process sealing shoulder when the sensor is inserted within the bore. First and second cam arms are rotatably mounted to the coupler between an unlocked position and a locked position. Each cam arm has a cam surface which faces the bore for engagement with the cam follower surface of the sensor.

BRIEF DESCRIPTION OF THE DRAWINGS

FIG. 5 shows a side plan view of a sensor and coupler according to an alternative embodiment of the present invention.

FIG. 6 shows a side plan view of the sensor inserted into the coupler of FIG. 5.

DETAILED DESCRIPTION OF THE PREFERRED EMBODIMENTS

Figure 1:
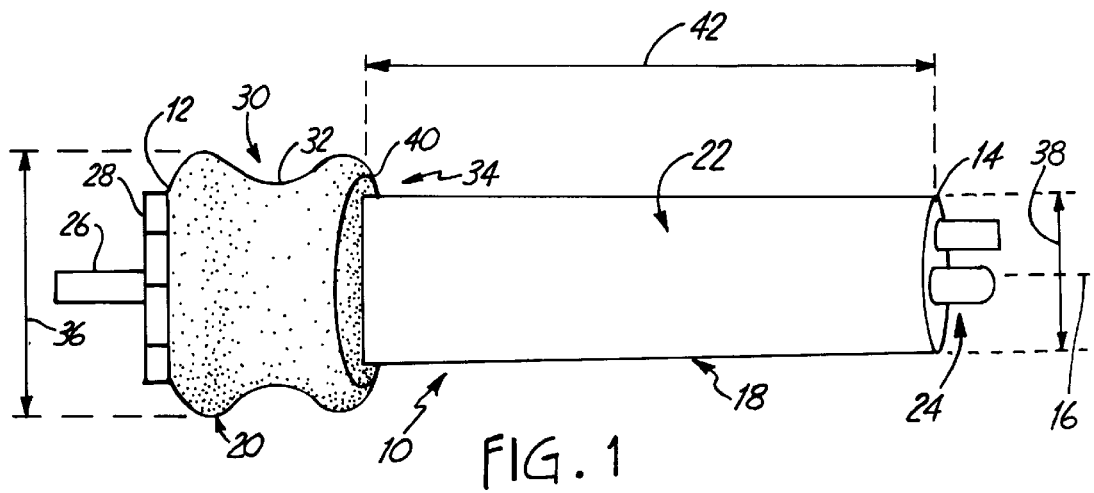
FIG. 1 shows a perspective view of an industrial process sensor according to one embodiment of the present invention.

FIGS. 1 shows a perspective view of an industrial process sensor according to one embodiment of the present invention. Sensor 10 includes proximal end 12, distal end 14, longitudinal axis 16, tubular sensor body 18 and adapter 20. Sensor body 18 and adapter 20 together define outer diameter surface 22 of sensor 10. Sensor body 18 and adapter 20 each have a generally cylindrical shape. Sensor body 18 carries sensor element 24 at distal end 14 for measuring a process variable in a sample solution, such as an aqueous process solution. For example, sensor element 24 can include an ion sensitive field effect transistor (ISFET), a pH sensor, an oxidation reduction potential (ORP) sensor, a selective ion sensor, a dissolve gas sensor, a conductivity sensor, a pressure sensor or a temperature sensor.

Cable 26 extends from proximal end 12 and is electrically coupled to sensor element 24 through measurement circuitry carried within sensor body 18. The measurement circuitry generates an electrical signal on cable 26, such as a voltage or current, having a characteristic representative of the measured variable.

Adapter 20 is positioned at proximal end 12 and provides a mounting feature for sensor 10. Adapter 20 is configured for mounting sensor 10 within a cam arm locking coupler which, in turn, is secured to the process through a pipe or tank fitting, for example. Adapter 20 and sensor body 18 can be incorporated into body 18 as a single, continuous piece of material with body 18 or can be formed of separate pieces of material which are secured together. In one embodiment, adapter 20 is attached to the outer diameter surface of sensor body 18 by a nut 28 which is threaded onto sensor body 18 at proximal end 12. Sensor body 18 has an increase in diameter (not shown) adjacent the inner diameter surface of adapter 20 which prevents axial movement of adapter 20 relative to nut 28.

Adapter 20 includes annular channel 30 which extends around a circumference of adapter 20. Channel 30 provides a cam follower surface 32 for engaging corresponding cam arms of the coupler as discussed with reference to FIG. 2. In one embodiment, cam follower surface 32 has a semicircular cross section as viewed within a plane that is parallel to and intersects longitudinal axis 16. Other cross-sectional shapes can also be used. Outer diameter surface 22 has a diameter reduction 34 from a maximum outside diameter 36 on adapter 20 to a minimum outside diameter 38 on sensor body 18. Diameter reduction 34 defines a process sealing shoulder 40 on adapter 20 which faces distal end 14. Shoulder 40 lies generally in a plane intersecting longitudinal axis 16. Sensor body 18 has a length 42 measured from shoulder 40 to distal end 14 which is selected to position sensor element 24 at a desired location within a process.

Figure 2:
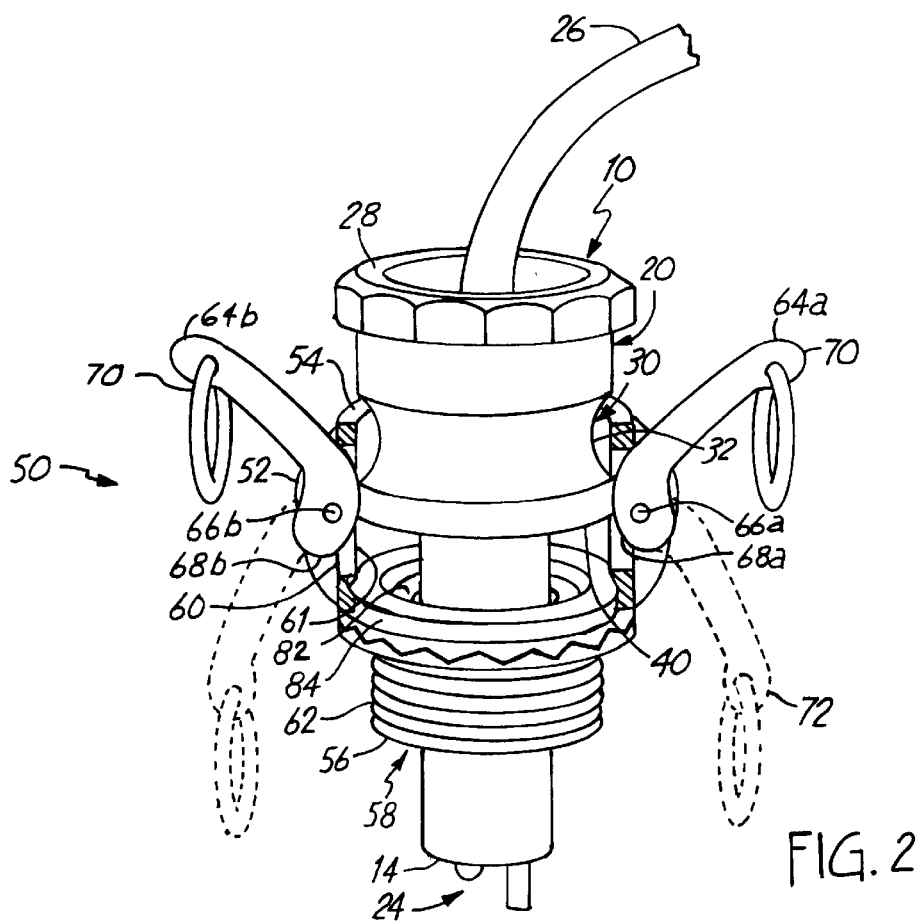
FIG. 2 shows a perspective view of the sensor partially inserted within a cam arm locking coupler.

FIG. 2 shows a perspective view of sensor 10 partially inserted within cam arm locking coupler 50. Portions of coupler 50 are cut away for clarity. Coupler 50 includes coupler body 52, proximal end 54, distal end 56, bore 58 which extends from proximal end 54 to distal end 56, outer diameter surface 60 and inner diameter surface 61. Male-type thread 62 is formed on outer diameter surface 60 at distal end 56 for coupling to a female-type thread of a process fitting. Other types of process connection features can also be used.

Cam arms 64a and 64b are pivotally mounted to coupler body 52 through pins 66a and 66b, respectively. Cam arms 64a and 64b include cam surfaces 68a and 68b, respectively, which extend through coupler body 52 and into central bore 58. Cam arms 64a and 64b pivot between an unlocked position 70 and a locked position 72 (shown in phantom). In unlocked position 70, cam surfaces 68a and 68b are substantially withdrawn from central bore 58. As cam arms 64a and 64b are pivoted from unlocked position 70 to locked position 72, cam surfaces 68a and 68b progressively enter central bore 58 and engage cam follower surface 32 on adapter 20 when sensor 10 is fully inserted within coupler 50.

Coupler 50 further includes a diameter reduction on inner diameter surface 61 which defines a process sealing shoulder 82 that faces shoulder 40 on adapter 20. An annular elastomeric seal 84 is positioned on shoulder 82 to provide a fluid tight seal between shoulder 82 and shoulder 40 when sensor 10 is fully inserted within coupler 50 and cam arms 64a and 64b are pivoted into their locked positions.

Shoulder 40 is preferably located with respect to channel 30 such that the full actuation of cam arms 64a and 64b act on channel 30, causing shoulder 40 to compress elastomeric seal 84. In one embodiment, maximum outside diameter 36 of sensor 10 forms a slip fit with the maximum inside diameter of coupler body 52, and minimum outside diameter 38 (shown in FIG. 1) forms a slip fit with the minimum inside diameter of coupler body 52.

In an alternative embodiment, sensor body 18 is equipped with O-rings or other peripheral seals for engaging the minimum or maximum inside diameter surfaces of coupler body 52 to provide additional sealing.

During installation, coupler 50 is first screwed into the process fitting through male threads 62. Cam arms 64a and 64b are pivoted to unlocked position 70. Sensor 10 is inserted into bore 58 until process sealing shoulder 40 on adapter 20 contacts elastomeric seal 84. This aligns channel 30 and cam follower surface 32 with cam surfaces 68a and 68b of cam arms 64a and 64b. Cam arms 64a and 64b are then pivoted from unlocked position 70 to locked position 72. As cam arms 64a and 64b are pivoted, cam surfaces 68a and 68b progressively engage cam follower surface 32 and force shoulder 40 in an axial direction against seal 84 to form a fluid-tight process seal. Removal of sensor 10 from coupler 50 is performed by a reverse operation. Coupler 50 can remain permanently or semi-permanently installed in the process piping.

Figure 3:
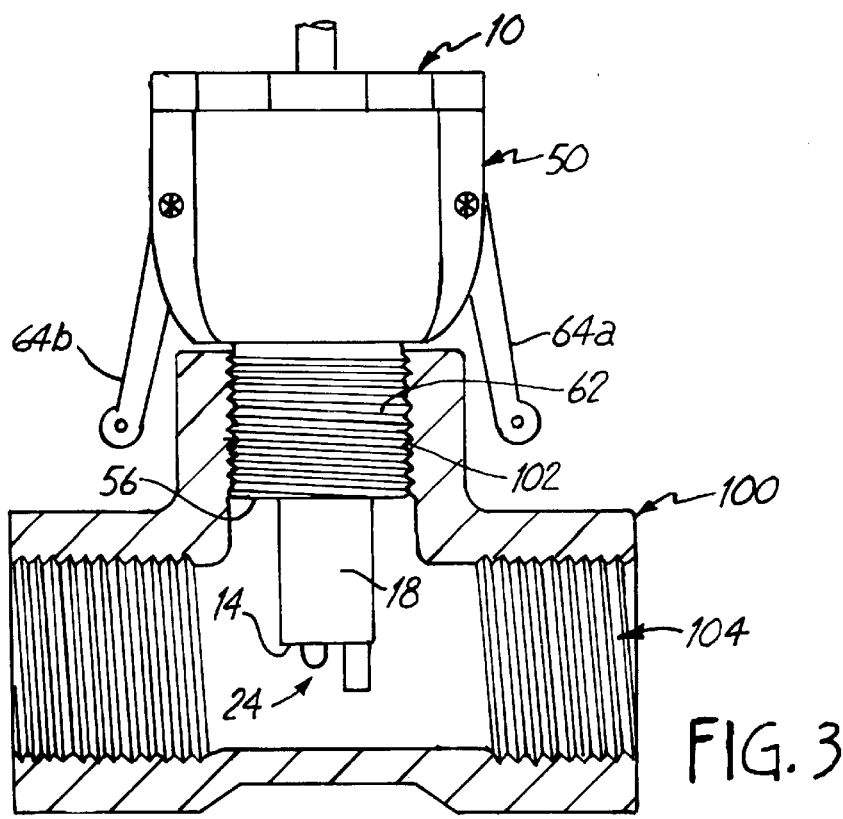
FIG. 3 shows a side plan view of the sensor and coupler mounted within a T-type process pipe fitting.
Figure 3A:
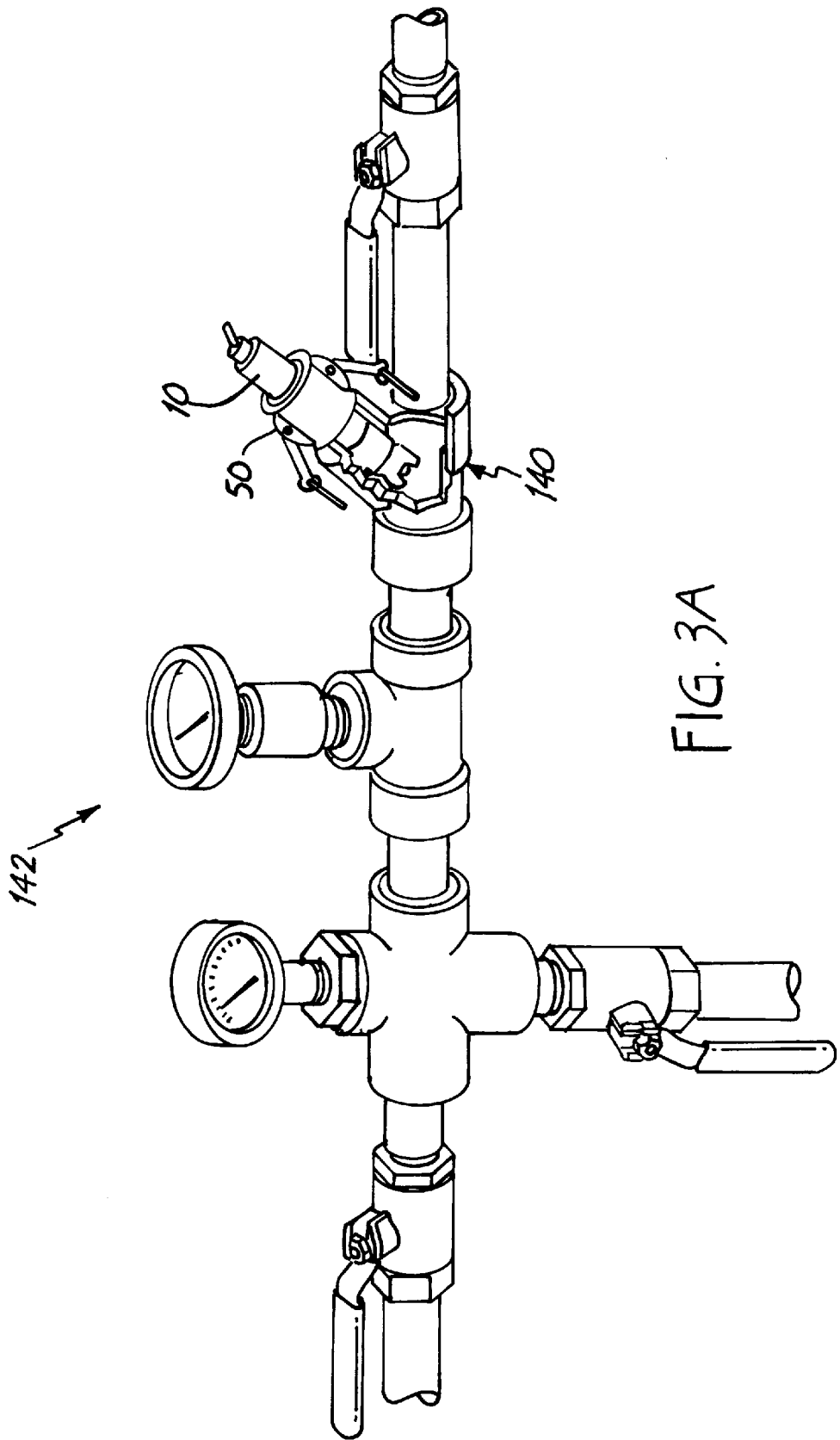
FIG. 3a shows the sensor and coupler mounted within an industrial process plant.

FIG. 3 shows a side plan view of sensor 10 and coupler 50 mounted within a T-type process pipe fitting 100. Pipe fitting 100 is shown in cross section. Male threads 62 of coupler 50 are threaded into female threads 102 of fitting 100. The length 42 of sensor body 10 is selected such that when sensor 10 is secured within coupler 50, sensor body 18 extends from distal end 56 of coupler 50 a distance sufficient to place sensor element 24 within bore 104 of fitting 100. FIG. 3a shows sensor 10 and coupler 50 mounted within a Y-type process fitting 140 in an industrial process plant 142.

Figure 4A:
FIGS. 4a–4i show enlarged, fragmentary views of a process sealing shoulder on the sensor, which illustrate alternative sealing face configurations.
Figure 4B:
Figure 4C:
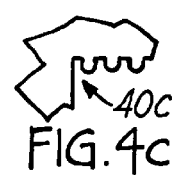
Figure 4D:
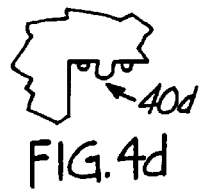
Figure 4E:
Figure 4F:
Figure 4G:
Figure 4H:
Figure 4I:
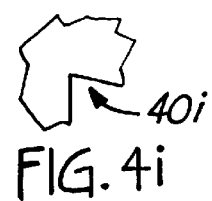

FIGS. 4a–4i show enlarged, fragmentary views of process sealing shoulder 40 which illustrate alternative sealing face configurations. In FIG. 4a, shoulder 40a has a substantially flat sealing face. In FIG. 4b, shoulder 40b has a channeled sealing face. In FIG. 4c, shoulder 40c has a ridged sealing face. In FIG. 4d, shoulder 40d has a sealing face with regularly or irregularly spaced bumps. In FIG. 4e, shoulder 40e has a concave sealing face. In FIG. 4f, shoulder 40f has a convex sealing face. In FIG. 4g, shoulder 40g has a curved, non-spherical sealing face. In FIGS. 4h and 4i, shoulders 40h and 40i have angled sealing faces. Any combination of two or more of the sealing face configurations shown in FIGS. 4a–4i can be used to minimize seal leakage, wear or compression set. These configurations can be used individually or together to insure a small, controlled leak upon any loss of seal compression. This would provide an early warning that the system is under pressure and that the cam arms should not be further released, but instead re-engaged until the system is unpressurized.

FIG. 5 shows a side plan view of a sensor and coupler according to an alternative embodiment of the present invention. Sensor 150 includes sensor body 152, adapter 154 and retaining ring 156. Sensor body 152 has a proximal end 158, a distal end 160 and an outer diameter surface 162 for receiving adapter 154. Outer diameter surface 162 has a diameter increase 164 for engaging a diameter increase 166 on inner diameter surface 168 of adapter 154. A retaining ring groove 170 is positioned between proximal 158 and diameter increase 164 for receiving retaining ring 156. Retaining ring 156 and diameter increase 164 together define the axial position of adapter 154 on sensor body 152. Outer diameter surface 162 further includes grooves 174 and 176 for receiving O-rings 176 and 178, respectively. O-rings 176 and 173 provide process sealing between sensor body 152 and inner diameter surface 168 of adapter 154.

Sensor body 152 carries sensor element 180 at distal end 160. Sensor element 180 is electrically coupled to cable 182. In one embodiment, sensor body 152 is formed of a highly chemical resistant prolyproylene material which is completely sealed to eliminate process intrusion. Adapter 154 can be formed of Polyetheretherkeytone, for example.

Coupler 190 has a proximal end 192, a distal end 194 and a central bore 196 for receiving sensor body 152 and adapter 154. Coupler 190 further includes cam arms 198 and 200 and locking spring 202. Cam arms 198 and 200 pivot between an unlocked position 203 and a locked position 204 (shown in phantom). Locking spring 202 biases cam arms 198 and 200 in locked position 204 to prevent accidental release of the cam arms, and also requires the use of both hands to release one cam arm at a time which may prevent the coupler from "blowing off" the process fitting if the process has not yet been depressurized. In one embodiment, sensor body 152 is configured for use with a commercially available Civacon 316 stainless steel TWIN-KAM® KAM-LOK® coupler. FIG. 6 shows a side plan view of sensor 150 inserted into coupler 190, with cam arms 198 and 200 in locked position 204.

The industrial process sensor of the present invention in combination with the cam arm locking coupler allows for a rapid fluid-tight sensor process insertion without the need to rotate the sensor. The present invention requires no tools, no multiple rotation of the fitting and no partial rotation of the sensor for insertion or removal of the sensor. The cam arms of the coupler are simply swung to the unlocked position to allow insertion of the sensor and then swung fully to the locked position to lock the sensor into place. The present invention significantly reduces plant maintenance by reducing insertion and removal time from about 10–15 minutes to about 30 seconds. The cam arm positions also provide a visually perceptible indication of a seal, and can be safely secured in the locked position by a bias spring or by wire straps.

Although the present invention has been described with reference to preferred embodiments, workers skilled in the art will recognize that changes may be made in form and detail without departing from the spirit and scope of the invention.

What is claimed is:

1. A quick-connect industrial process sensor comprising:
    a proximal end, a distal end, a longitudinal axis and an outer diameter surface;
    a cam follower surface recessed into the outer diameter surface;
    a diameter reduction on the outer diameter surface, between the cam follower surface and the distal end, which defines a process sealing shoulder that faces the distal end; and
    a sensor element carried at the distal end.

2. The quick-connect industrial process sensor of claim 1 and further comprising:
    a sensor body and an adapter secured to the sensor body which together define the outer diameter surface of the sensor; and
    wherein the cam follower surface is recessed into the adapter, the diameter reduction is defined by a reduction in diameter from the adapter to the sensor body and the process sealing shoulder is formed by a distal surface of the adapter.

3. The quick-connect industrial process sensor of claim 1 wherein the cam follower surface has a semi-circular cross section within a plane that is parallel to and intersects the longitudinal axis.

4. The quick-connect industrial process sensor of claim 1 wherein the outer diameter surface has a generally cylindrical shape and a circumference and wherein the cam follower surface comprises an annular channel which extends around the circumference.

5. The quick-connect industrial process sensor of claim 1 wherein the process sealing shoulder comprises a surface selected from the group consisting of a flat surface, a concentrically channeled surface, a concentrically ridged surface, a textured surface, a concave surface, a convex surface, a curved non-spherical surface, an angled surface, a positively chamfered surface and a negatively chamfered surface.

6. The quick-connect industrial process sensor of claim 1 and further comprising:
    a circumference;
    a radial process sealing channel formed in the outer diameter surface between the process sealing shoulder and the distal end and extending around the circumference; and
    an annular elastomeric seal positioned within the radial process sealing channel.

7. The quick-connect industrial process sensor of claim 1 wherein the sensor element is selected from the group consisting of an ion sensitive field effect transistor (ISFET), an oxidation reduction potential sensor, a selective ion sensor, a dissolved gas sensor, a conductivity sensor, a pressure sensor and a temperature sensor.

8. The quick-connect industrial process sensor of claim 1 wherein the process sealing shoulder lies in a plane intersecting the longitudinal axis.

9. The quick-connect industrial process sensor of claim 1 and further comprising a cable electrically coupled to the sensor element and extending from the proximal end.

10. A sensor mounting kit comprising:
    an industrial process sensor comprising: proximal and distal ends, a longitudinal axis and an outer diameter surface; a cam follower surface recessed into the outer diameter surface of the sensor; a first diameter reduction on the outer diameter surface of the sensor, between the cam follower surface and the distal end of the sensor, which defines a first process sealing shoulder that faces the distal end of the sensor; and a sensor element carried at the distal end of the sensor; and
    a process coupler comprising: a coupler body comprising a proximal end, a distal end, a bore extending from the proximal end to the distal end of the coupler body, an inner diameter surface adjacent the bore and an outer diameter surface; a second diameter reduction on the inner diameter surface and defining a second process sealing shoulder which engages the first process sealing shoulder when the sensor is inserted within the bore; a cam arm pivotally mounted to the coupler body between an unlocked position and a locked position and having a cam surface which faces the bore, wherein the cam surface is disengaged from the cam follower surface when the sensor is inserted within the bore and the cam arm is in the unlocked position and progressively engages the cam follower surface when the cam arm is pivoted from the unlocked position to the locked position; and a process connection feature formed on the coupler body, adjacent the distal end of the coupler body.

11. The sensor mounting kit of claim 10 wherein the sensor further comprises:
    a sensor body and an adapter secured to the sensor body which together define the outer diameter surface of the sensor; and
    wherein the cam follower surface is recessed into the adapter, the first diameter reduction is defined by a reduction in diameter from the adapter to the sensor body and the first process sealing shoulder is formed by a distal surface of the adapter.

12. The sensor mounting kit of claim 10 wherein the cam follower surface has a semi-circular cross section within a plane that is parallel to and intersects the longitudinal axis.

13. The sensor mounting kit of claim 10 wherein the outer diameter surface of the sensor body has a generally cylindrical shape and a circumference and wherein the cam follower surface comprises an annular channel which extends around the circumference.

14. The sensor mounting kit of claim 10 wherein the cam surface applies an axial force on the cam follower surface which forces the first process sealing shoulder against the second process sealing shoulder when the cam arm is in the locked position.

15. The sensor mounting kit of claim 10 and further comprising an annular elastomeric seal positioned between the first and second process sealing shoulders.

16. The sensor mounting kit of claim 10 wherein the sensor has a length measured from the first process sealing shoulder to the distal end of the sensor such that the distal end of the sensor and the sensor element carried at the distal end of the sensor extend beyond the distal end of the process coupler when the sensor is inserted into the bore until the first process sealing shoulder engages the second process sealing shoulder.

17. The sensor mounting kit of claim 10 wherein the sensor has a maximum outside diameter, the process coupling has a maximum inside diameter, and the maximum outside diameter of the sensor forms a slip fit with the maximum inside diameter of the process coupler.

18. The sensor mounting kit of claim 10 wherein the sensor has a minimum outside diameter, the process coupling has a minimum inside diameter, and the minimum outside diamete of the sensor forms a slip fit with the minimum inside diameter of the process coupler.

19. An industrial process sensing apparatus comprising:

a process fitting;

a process coupler comprising: a coupler body and a bore extending through the coupler body; a process connection feature formed on the coupler body and secured to the fitting; a first diameter reduction on the coupler body within the bore which defines a first process sealing shoulder; and a cam arms pivotally mounted to the coupler body between an unlocked position and a locked position, the cam arm having a cam surface which faces the bore which is withdrawn from the bore when the cam arm is in the unlocked position and progressively enters the bore when the cam arm is pivoted from the unlocked position to the locked position; and an industrial process sensor extending through the bore and comprising: an cuter diameter surface having a circumference; a second diameter reduction on the outer diameter surface which defines a second process sealing shoulder that faces the first process Dealing shoulder; and a channel recessed into the outer diameter surface along the circumference and positioned relative to the second process sealing shoulder such that the cam surface engages the channel when the cam arm is in the locked position and forces the second process sealing shoulder against the first process sealing shoulder to form a process seal.

* * * * *

UNITED STATES PATENT AND TRADEMARK OFFICE
CERTIFICATE OF CORRECTION

PATENT NO. : 6,000,290
DATED : December 14, 1999
INVENTOR(S) : Barry W. Benton et al.

It is certified that error appears in the above-identified patent and that said Letters Patent is hereby corrected as shown below:

<u>Column 8,</u>
Line 5, delete "cuter" and insert --outer--.
Line 8, delete "Dealing" and insert --sealing--.

Signed and Sealed this

Twenty-sixth Day of June, 2001

*Attest:*

*Attesting Officer*

NICHOLAS P. GODICI
*Acting Director of the United States Patent and Trademark Office*